Figure 1:
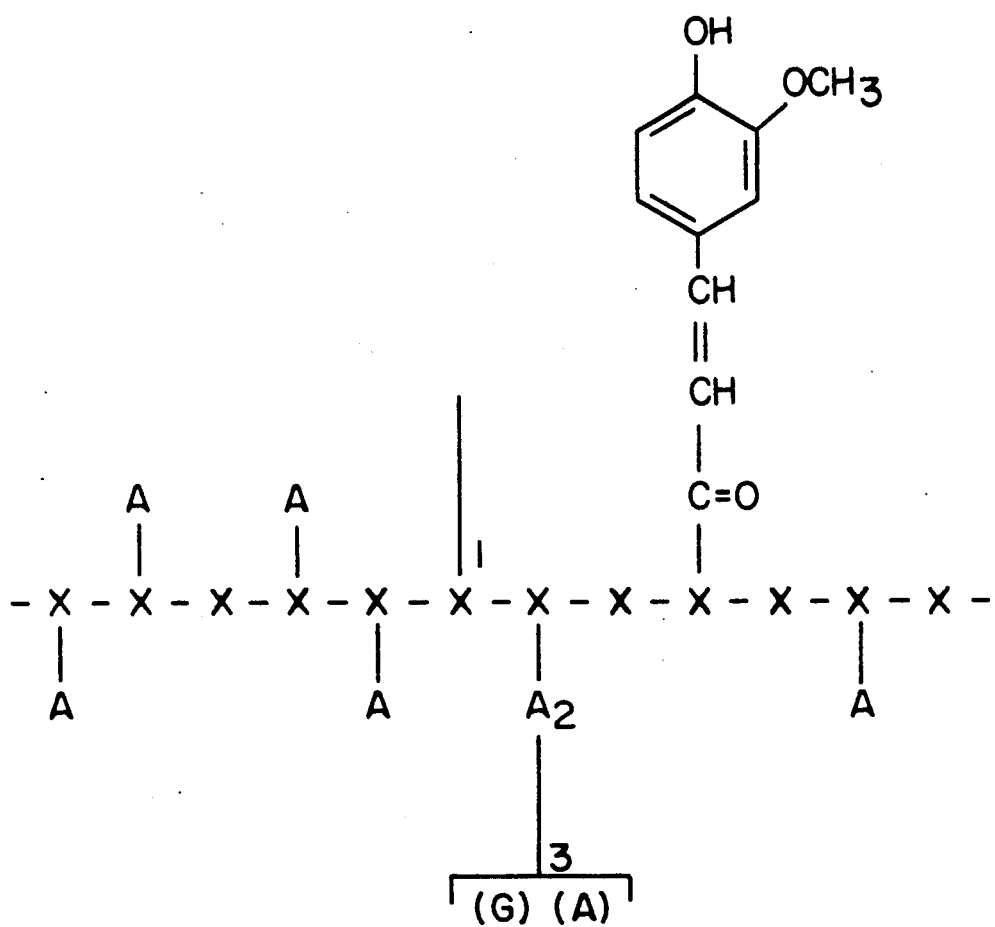

United States Patent [19]

Ducroo

[11] Patent Number: 5,023,176
[45] Date of Patent: * Jun. 11, 1991

[54] PRODUCTION OF GLUCOSE SYRUPS AND PURIFIED STARCHES FROM WHEAT AND OTHER CEREAL STARCHES CONTAINING PENTOSANS

[75] Inventor: Paul Ducroo, Phalempin, France

[73] Assignee: Gist-Brocades N.V., Delft, Netherlands

[*] Notice: The portion of the term of this patent subsequent to May 24, 2005 has been disclaimed.

[21] Appl. No.: 936,802

[22] Filed: Dec. 2, 1986

[30] Foreign Application Priority Data

Dec. 3, 1985 [EP] European Pat. Off. ........ 85202016.3

[51] Int. Cl.$^5$ .................. C12P 19/02; C12C 9/00; C12N 9/24; C12N 9/28
[52] U.S. Cl. .................................. 435/105; 435/200; 435/202; 435/203; 435/911; 435/917; 426/28
[58] Field of Search ............... 435/105, 200, 202, 203, 435/917, 911; 426/28, 62, 661

[56] References Cited

U.S. PATENT DOCUMENTS 4,746,517 5/1988 Ducroo .............................. 435/911

FOREIGN PATENT DOCUMENTS 2150933 7/1985 United Kingdom .

OTHER PUBLICATIONS

Udea et al., "Production of Ethanol from Raw Cassava Starch by a Nonconventional Fermentation Method", Biotech Bioeng VXXIII, 1981, 291-99.
Comtat et al., "Mode of Action of a Xylanase and its Significance for the Structural Investigation of the Branched L-Arabino-D-Glucarono-D-Xylan from Redwood", Carb. Res. Ja5, 101-112, 1981.

Primary Examiner—Elizabeth C. Weimar
Assistant Examiner—Gail Poulos
Attorney, Agent, or Firm—Bierman and Muserlian

[57] ABSTRACT

The filterability of glucose syrups obtained from impure wheat or other cereal starch is improved by treatment with Disporotrichum. Also the separation of starch from other constituents of impure cereal starch is improved by addition of xylanase before the starch is separated.

5 Claims, 4 Drawing Sheets

PRODUCTION OF GLUCOSE SYRUPS AND PURIFIED STARCHES FROM WHEAT AND OTHER CEREAL STARCHES CONTAINING PENTOSANS

The invention relates to the preparation of glucose syrups from unpurified wheat and other cereal starches containing pentosans and to the separation of such starches from other cereal constituents, for example gluten.

Cellulose and starch are the most abundant sources of carbohydrates. Because starch is much more readily accessible to the human digestive system than cellulose it has a long history as a food-stuff. It is also an important industrial raw material.

In principle starch can be depolymerized under the catalytic effect of acids but this route leads to a rather incomplete depolymerization and the formation of rather large amounts of by-products. Enzymatic hydrolysis of starch has therefore been receiving increasing attention.

Natural starch is known to contain two types of macromolecule composed of glucose units. One type of molecule, called amylose, is linear and consists exclusively of alpha,1-4 linked glucose units. Starch contains about 25% of amylose. The second type of molecule, amylopectin, is highly branched and contains alpha,1-4 as well as alpha,1-6 linked glucose units. The overall content of alpha,1-6 linkages is generally less than 5%.

In modern industrial starch degradation two types of enzyme are in common use. The enzyme alpha-amylase is used for the liquefaction (or thinning) of starch into dextrins having an average degree of polymerization of about 7-10, and the enzyme amyloglucosidase is used for the final saccharification, resulting in a syrup of high glucose content (92-96%).

Cereals such as wheat and barley contain gums which increase the viscosity and reduce the filterability of aqueous extracts of the cereals including glucose syrups made in the manner just described and purified starches themselves. Such gums consist mainly of glucans, but also contain some pentosans. The structure of pentosans is more complicated than the usually presented structure with long chains of 1,4-beta-D-xylopyranose and single 1,2- or 1,3-alpha-L-arabinofuranose side groups (in the ratio of 1 to 2 xylose units); see FIG. 1 of the accompanying drawings, taken from H. Neukom, L. Providoli, H. Gremli and P. A. Jui, Cereal Chem., 44, 238 (1967).

The properties of pentosans vary with the presence or absence of peptides, ferulic acid and arabinogalactan. About ⅔ of total pentosans are insoluble because of their high molecular weight and some interlinkages with proteins and other constituents. They have a very high water retention power and give very bulky spent filtration cakes. When arabinofuranose side groups of soluble pentosans are hydrolysed, an association and precipitation of non-substituted xylans is observed.

The average pentosan content of various cereals is as follows (see "Handbuch der Lebensmittelchemie", Vol. 5, p. 32, 1967, Springer Verlag):

| Cereal grain | Pentosans (% dry weight) |
| --- | --- |
| Barley (incl. husks) | 10.3 |
| Wheat | 7.4 |
| Rye | 10.6 |
| Oats (incl. husks) | 7.5 |
| Corn | 6.2 |
| Rice | 2.0 |
| Millet | 2.0 |

In order to improve the filterability of glucose syrups obtained from unpurified wheat starch, treatment of the syrup with xylanase has been tried. Xylanase is an enzyme which hydrolyses xylans which occur in pentosans.

In Starch 36, 135 (1984), a beta-glucanase product of fungal origin is described which possesses pentosanase activity. This enzyme is recommended for the treatment of waste water from the wheat starch industry.

British Specification No. 2,150,933 describes a pentosanase obtained by fermentation of Talaromyces (i.e. Penicillium) emersonii. This enzyme is stated to be capable of catalysing the degradation of xylan and to be useful, inter alia, for reducing the viscosity of starch slurries to improve starch recovery.

According to the present invention, glucose syrups of improved filterability and/or lower viscosity are produced from impure cereal starch containing pentosans by a process, which comprises subjecting the said impure starch to the action of Disporotrichum xylanase to hydrolyse pentosans and to a hydrolysis to convert starch into glucose.

Thus the preparation of a glucose syrup from unpurified wheat starch may be improved by hydrolysing the starch with an enzyme mixture which contains, in addition to alpha-amylase and/or amyloglucosidase, also Disporotrichum xylanase.

The xylanase can also be used in the recovery of starch from wheat or other flours obtained from cereals containing pentosans. In the wet milling of wheat, gluten is separated from other constituents (starch slurry) mechanically. The starch slurry separates into a tightly packed lower layer of purified starch and a supernatant mucilaginous material. This mucilaginous fraction which contains small starch granules, hemicellulose and protein, has been called squeegee, tailings or sludge. The hemicellulose portion contains xylose (about 60%) arabinose (about 38%) and glucose (about 2%).

By passing wheat starch slurry through a continuous centrifuge, producers are able to separate the purer concentrate or "A" starch stream while the small grains together with swollen damaged grains and pentosan complexes form the impure or "B" starch stream. After previous treatment of the wheat starch slurry with Disporotrichum xylanase before passage through the continuous centrifuge, the yield of "A" quality starch is increased by hydrolysis of the pentosans and reduction of the viscosity of the tailings.

The xylanase used in the present invention is an endo-xylanase obtained from the Basidiomycete Disporotrichum and specifically Disporotrichum dimorphosporum, described in a revision of the genus Sporotrichum by J. A. Stalpers, Studies in Mycology, 24, 1 (1984).

Preferably, a xylanase preparation is used derived from Disporotrichum dimorphosporum. Very satisfactory results are obtained when using a xylanase preparation derived from Disporotrichum dimorphosporum strain ATCC 24562, available from the American Type Culture Collection, 12301 Parklawn Drive, Rockville, Md., which is identical with strain CBS 484.76, available from the Centraal Bureau voor Schimmelcultures, Oesterstraat 1, 3742 SK Baarn, Netherlands. These strains are preferred for the purpose of this invention.

Other xylanase preparations which may be used according to the present invention are those having substantially the same characteristics as the xylanase preparation which is obtainable from *Disporotrichum dimorphosporum* strain ATCC 24562 (or CBS 484.76). This includes preparations obtained from a transformed host microorganism containing the gene coding for the xylanase produced by said Disporotrichum strain ATCC 24562 (or CBS 484.76).

By culturing on a medium containing cellulose, pectin yeast extracts and different salts, *Disporotrichum dimorphosporum* produces an endo-xylanase. Endo-xylanase hydrolyses the 1,4-beta-xylose bindings within the pentosan chains. From a technical point of view, an endo-type enzyme is generally preferable because it hydrolyses high molecular weight polysaccharides very rapidly. An exo-type enzyme requires more time and more enzymatic concentration in order to reach the same technological result.

In our co-pending patent application Ser. No. 936,806 filed Dec. 2, 1986, now U.S. Pat. No. 4,746,517, and based on European patent application 85202016.3 of Dec. 3, 1985, a method is disclosed for determining endo-xylanase activity. This application is herein incorporated by reference.

A concentrate of Disporotrichum xylanase suitable for use in the present invention may be obtained in the following manner. The fermentation is carried out in a sterile tank and medium in known manner. The culture medium contains cellulose, pectin, yeast extract and appropriate salts. It is inoculated with a pure culture of *Disporotrichum dimorphosporum*. The fermentation is effected at a constant temperature between 20° C. and 37° C., preferably about 32° C., and the pH is maintained within the range of 3.0 and 6.0, preferably 4.0 to 4.5. The fermentation can be batchwise or continuous. The xylanase activity is followed during the process. It is not necessary to induce the production of the enzyme by addition of xylan-containing materials (e.g. corn cobs or flours), and the addition of such products mainly promotes the formation of an exo-xylanase, which is less useful for the invention. When the required enzymatic activity has been reached the mash is harvested, filtered and concentrated by vacuum concentration or ultrafiltration. The concentrate can be sold as a liquid preparation or spray dried in a powder form. The endoxylanase hydrolyses the 1,4-beta-xylose linkages within the pentosan chains.

Figure 2:
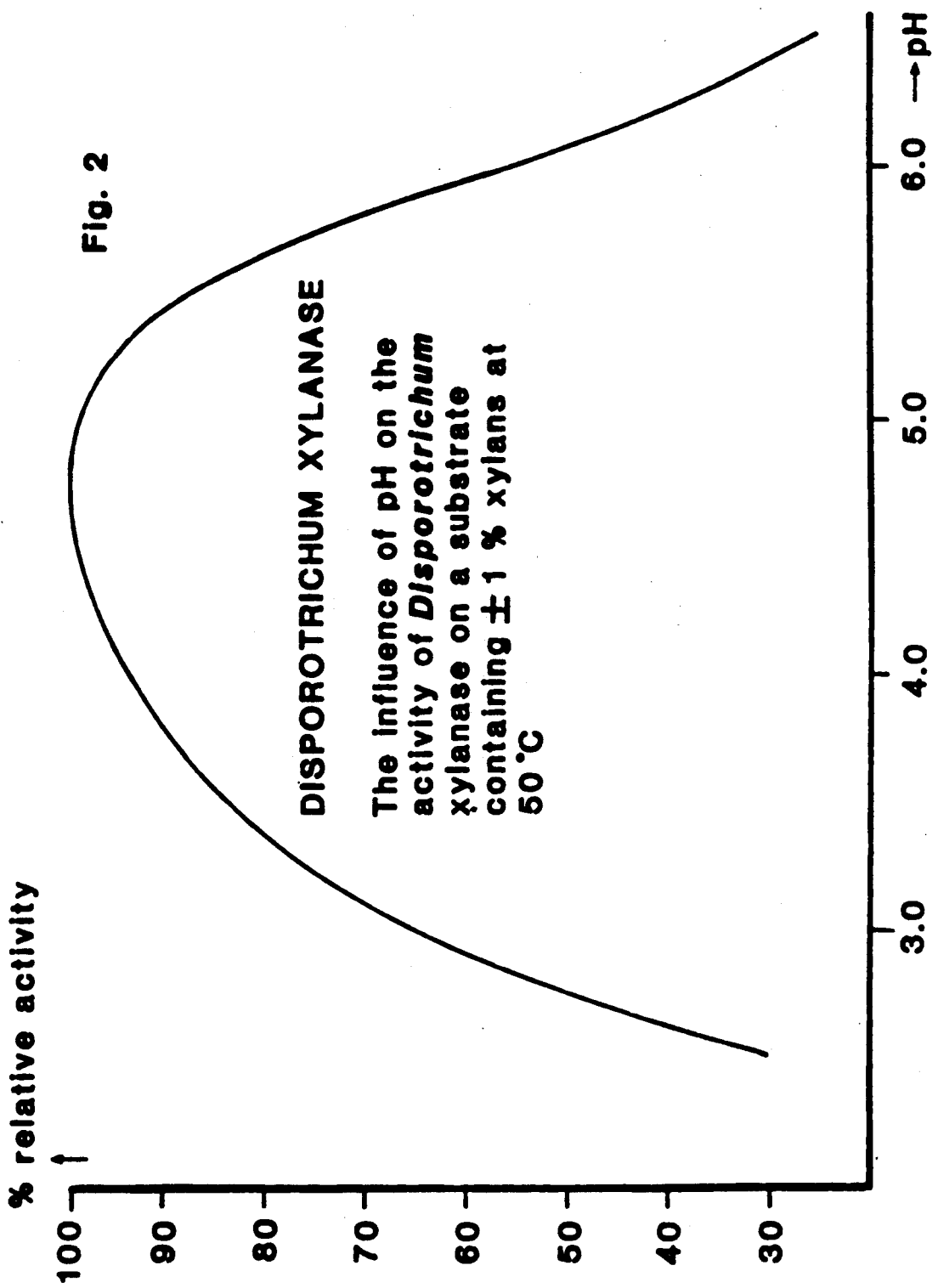
Figure 3:
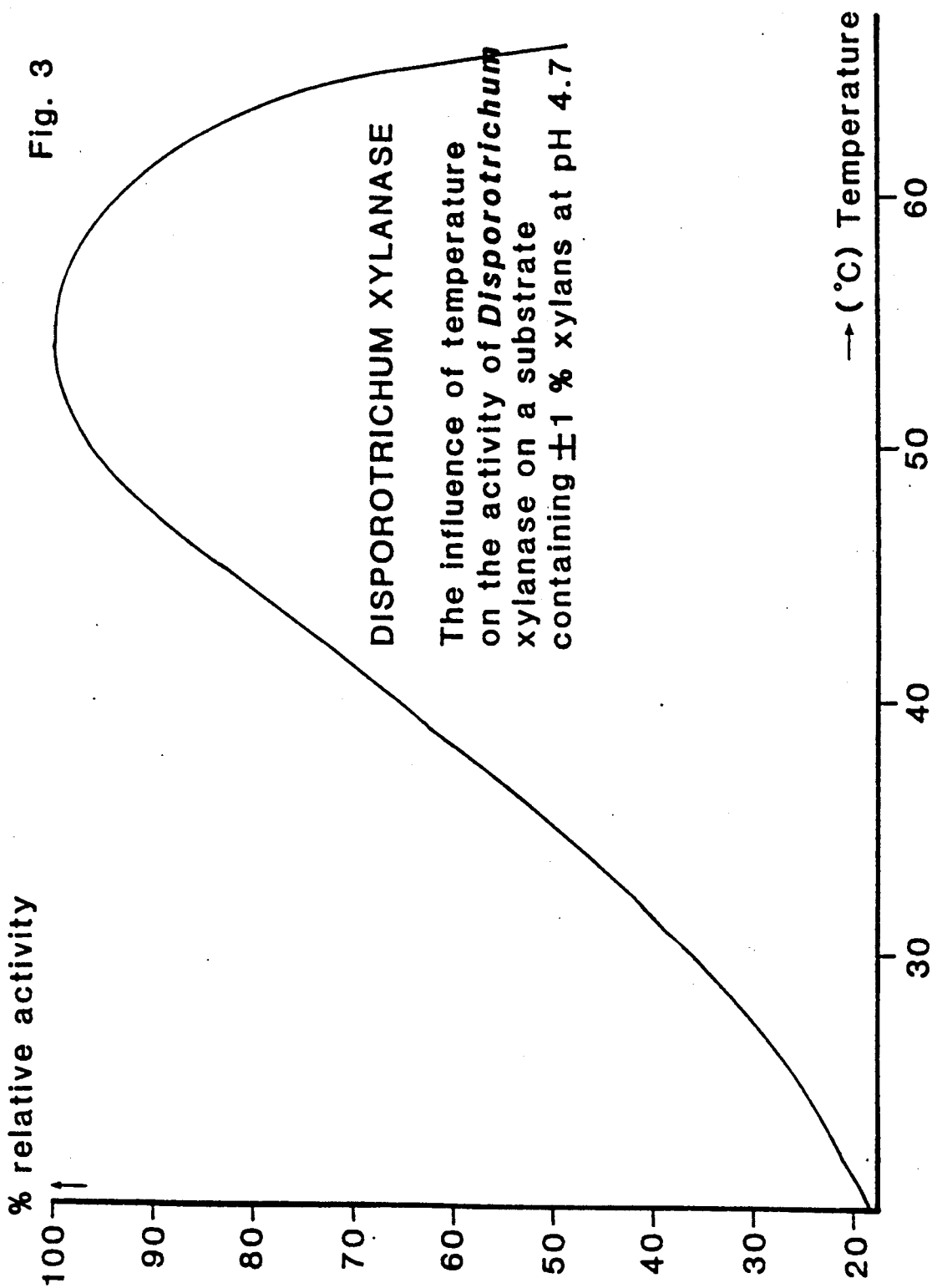

The properties of the non-purified enzymatic product have been studied viscosimetrically with a substrate containing ±1% xylans (see accompanying FIGS. 2 ad 3) The optimum pH is 4.7, but between pH 3.0 and 6.0 the relative activity is more than 50%. The optimum temperature is 55° C. but more than 50% relative activity remains at 65° C. Purification of this Disporotrichum xylanase was studied by Comtat et al. (J. Comtat, K. Ruel, J.-P. Joseleau and F. Barnoud, Symposium on Enzymatic Hydrolysis of Cellulose, S.I.T.R.A., Helsinki, Finland, 351 (1975); J. Comtat and J.-P. Joseleau, Carbohydr. Res., 95, 101 (1981)).

When the influence of enzymes with endo- and exo-xylanase activity on the filterability of glucose syrups made from unpurified wheat starch was investigated, it was found that Sumizym AC (*Aspergillus niger* cellulase from Shin Nihon), Drum pectinase (*Aspergillus niger* drum pectinase from Gist-brocades) and Disporotrichum xylanase were very active. Results obtained with Sumizym AC are highly dependent on enzymatic concentration, but the results obtained with Disporotrichum xylanase are not. It appears that Sumizym AC is only effective by its exo-enzymatic activity and Disporotrichum only by its endo-enzymatic activity.

The total effect of Disporotrichum xylanase is apparently obtained at low concentration. Drum pectinase and Sumizym AC have about the same efficiency but Drum pectinase gives more glucose reversion.

Disporotrichum endo-xylanase and *Penicillium emersonii* endo-xylanase were compared by addition of the same quantities of exo-xylanase activity from *Aspergillus niger* products. *P. emersonii* xylanase and exo-xylanase blends show a smaller effect than Disporotrichum xylanase and exo-xylanase blends.

The following Examples illustrate the invention.

EXAMPLE I

Standard procedure for liquefaction, saccharification and filtration of type B wheat starch As substrate, type B wheat starch from Roquette Freres, reference LAB 833, containing about 1.2–1.5% proteins and 3–4% pentosans, was used.

A. Liquefaction process

Wheat starch was liquefied at 30% D.S. in well water 160 ppm $Ca^{++}$) in a liquefaction pilot plant according to the following process:

6 minutes at 105°–106° C.

2 hours at 95° C.

We have used 6 units of Maxamyl, a thermostable *Bacillus licheniformis* alpha-amylase from Gist-Brocades, was not possible to liquefy at higher D.S. because the per gram of D.S. The pH was corrected to 6.4 with NaOH. It was not possible to liquefy at higher D.S. because the slurry was very viscous.

B. Saccharification process

The pH of liquefied starch was corrected to 4.2. For the first experiments, 25000 AGI of Amigase GM (an Aspergillus niger amyloglucosidase from Gist-brocades) per kg D.S. was used. This extra dosage was chosen to avoid interference of starch retrogradation on the filtration tests. The last experiments were realized with the normal 17500 AGI/kg D.S.

Filtration enzymes have been added with the Amigase at the beginning of saccharification.

After 3 days at 60° C., the filterability was tested.

C. Filtration tests and analysis

A Seitz laboratory filter maintained at 60° C. by water circulation, equipped with a cloth filter, Dicalite 4258 S2 (Kieselguhr), was used. A precoat was made with 15 g of Dicalite 4258 S2 dispersed into 150 ml glucose syrup at 30% D.S. The saccharified starch was filtered under 1 bar pressure and the volume of filtrate per unit time was measured. A coefficient of filterability was obtained from the formula:

$$\frac{\text{vol. of filtrate after 15 min} - \text{vol. of filtrate after 1 min}}{14} =$$

volume of filtrate per min.

After filtration, the viscosity was measured in a capillary viscosimeter at 20° C. and HPLC analysis was used for determination of sugars.

EXAMPLE II

Improvement of the filtration of liquefied wheat starch by the addition of Disporotrichum xylanase Type B wheat starch containing 2–3% pentosans was liquefied by the traditional process used for corn starch syrup with 1° liquefaction of solid starch with alpha-amylase and 2° saccharification of the resulting liquefied starch with amyloglucosidase. This gave a syrup of high glucose content. Disporotrichum xylanase was introduced at the saccharification stage in addition to the amyloglucosidase.

Figure 4:
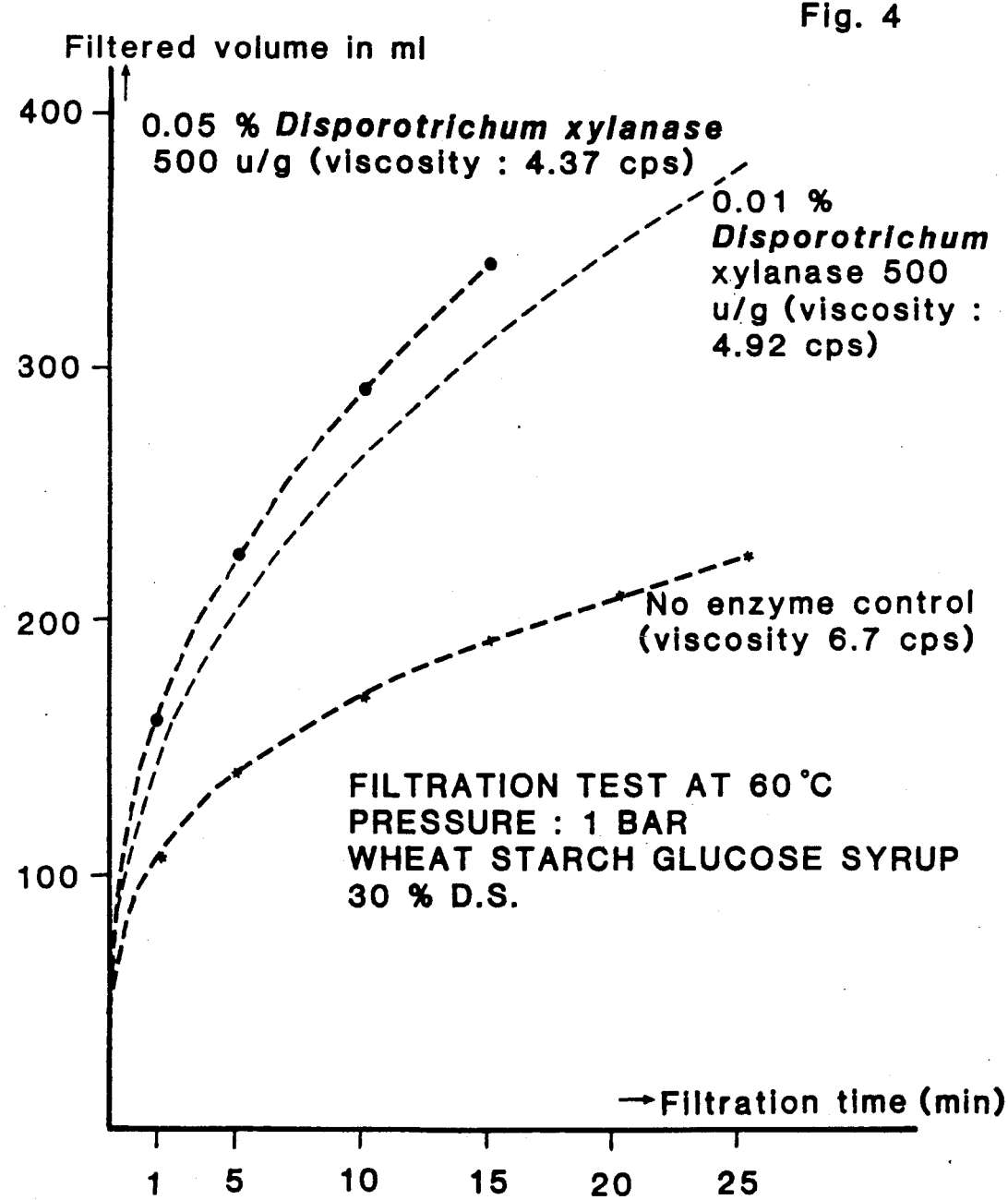

After three days of incubation at 60° C. and a pH of 4.2–4.5, filtration tests were carried out under standard conditions. The results, which are given in FIG. 4, show that the addition of Disporotrichum xylanase decreases the syrup viscosity, and thus improves the filterability.

EXAMPLE III

The activity of Disporotrichum xylanase and Sumizym AC on the filtration of liquefied type B wheat starch Conditions as in Example I, with 25000 AGI/kg D.S.

| enzyme | dosage in % D.S. | volume of filtrate per minute |
|---|---|---|
| Blank (only AG) | — | 7,8 ml |
| Disporotrichum xylanase | | |
| diluted to 500 u/g | 0.05 | 15.6 ml |
| diluted to 500 u/g | 0.1 | 15.2 ml |
| diluted to 500 u/g | 0.2 | 16.3 ml |
| Sumizym AC | 0.005 | 15.3 ml |
| Sumizym AC | 0.01 | 18.3 ml |
| Sumizym AC | 0.02 | 21.8 ml |
| Sumizym AC | 0.05 | 24.5 ml |

Results obtained with Sumizym AC are highly dependent on enzymatic concentration, but the results obtained with Disporotrichum xylanase are not.

EXAMPLE IV

The activity of Disporotrichum xylanase + Sumizym AC or Drum pectinase blends on the filtration of liquefied type B wheat starch Conditions as in Example I, with 25000 AGI/kg D.S.

| first enzyme | dosage % on D.S. | second enzyme | dosage % on D.S. | vol of filtrate per minute |
|---|---|---|---|---|
| blank | — | — | — | 7.5 ml |
| Disporo trichum xylanase | 0.005 | — | — | 12.9 ml |
|  | 0.01 | — | — | 14.0 ml |
|  | 0.02 | — | — | 14.8 ml |
| diluted to 500 u/g | 0.05 | — | — | 15.5 ml |
| diluted to 500 u/g | 0.05 | Sumizym AC | 0.005 | 18.5 ml |
| diluted to 500 u/g | " | Sumizym AC | 0.01 | 21.0 ml |
| diluted to 500 u/g | " | Sumizym AC | 0.02 | 20.8 ml |
| diluted to 500 u/g | " | Drum pect. | 0.005 | 17.7 ml |
| diluted | " | " | 0.01 | 20.5 ml |
| diluted to 500 u/g | " | " | 0.02 | 21.4 ml |

The total efficiency of Disporotrichum xylanase is obtained at low concentration. When used with this endo-xylanase, exo-xylanases from Drum pectinase and Sumizym AC have about the same efficiency but Drum pectinase gives more glucose reversion.

EXAMPLE V

The activity and glucose yield of Disporotrichum xylanase + Sumizym AC or Drum pectinase blends on the filtration of liquefied type B wheat starch Conditions as in Example I with 25000 AGI/kg D.S. (for results see Table on next page)

| first enzyme | dosage % on D.S. | second enzyme | dosage % on D.S. | vol. of filtrate per min (ml) | viscosity (mPa/s) | glucose yield (%) |
|---|---|---|---|---|---|---|
| blank (with AG) | — | — | — | 6.40 | 6.8 | — |
| Disporotrichum xylanase | | | | | | |
| diluted to 500 u/g | 0.01 | — | — | 11.20 | 4.45 | — |
| diluted to 500 u/g | " | Drum p. | 0.005 | 14.80 | 3.71 | 91.49 |
| diluted to 500 u/g | " | " | 0.0075 | 15.20 | 3.72 | 90.67 |
| diluted to 500 u/g | " | " | 0.01 | 16.4 | 3.71 | 90.40 |
| diluted to 500 u/g | " | " | 0.0125 | 16.8 | 3.69 | 90.02 |
| diluted to 500 u/g | " | Sumizym AC | 0.01 | 17.5 | 3.59 | 91.96 |

This experiment confirms the high reversion effect on glucose yield of Drum pectinase. The test with Sumizym AC was carried out for comparison.

EXAMPLE VI

The activities of Disporotrichum xylanase and Penicilium emersonil beta-glucanase with the same addition of exo-xylanase activity Conditions as in Example I, with 17500 AGI/kg D.S.

| first enzyme | dosage % on D.S. | second enzyme | dosage % on D.S. | vol. of filtrate per min (ml) | viscosity (mPa/s) | glucose yield (%) |
|---|---|---|---|---|---|---|
| blank (with AG) | — | — | — | 3.5 | 6.83 | 93.13 |
| Disporotrichum | 0.01 | — | — | 9.9 | 4.40 | 92.17 |
|  | " | Drum p. | 0.005 | 15.2 | 4.22 | 90.97 |

-continued

| first enzyme | dosage % on D.S. | second enzyme | dosage % on D.S. | vol. of filtrate per min (ml) | viscosity (mPa/s) | glucose yield (%) |
|---|---|---|---|---|---|---|
| xylanase diluted to 500 u/g | " | Sumizym AC | 0.0035 | 15.4 | 4.12 | 91.58 |
| P. emersonii | 0.02 | — | — | 9.0 | 4.67 | 92.28 |
| " | " | Drum p. | 0.005 | 11.7 | 4.35 | 90.96 |
| beta-glucanase | " | Sumizym AC | 0.0035 | 11.8 | 4.22 | 91.74 |

These experiments show a lower synergic effect for *P. emersonii* beta-glucanase endo-xylanase+exo-xylanase blends in comparison with Disporotrichum xylanase+exo-xylanase blends.

What I claim is:

1. In a process of producing a glucose syrup of improved filterability and lower viscosity by enzymatic hydrolysis of impure cereal starch containing pentosans, the improvement comprising using as the enzyme xylanase produced by *Disporotrichum dimorphosphorum* to hydrolyse pentosans and subjecting the product to hydrolysis to convert starch into glucose.

2. The process of claim 1 wherein glucose syrup is produced by subjecting impure wheat starch to the action of alpha-amylase and/or amyloglucosidase, and the said xylanase.

3. The process of claim 1 wherein the said xylanase is derived from *Disporotrichum dimorphosphorum* ATCC 24562.

4. The process of claim 1 wherein the xylanase is used in admixture with *Aspergillus niger* exo-xylanase.

5. In a process of separating a cereal starch from other constituents of the cereal, the improvement comprising subjecting a crude slurry of cereal starch to the action of xylanase produced by *Disporotrichum dimorphosporum* before the starch is separated mechanically from the other constituents of the slurry.

* * * * *